(12) United States Patent
Zalenski et al.

(10) Patent No.: US 9,072,610 B2
(45) Date of Patent: Jul. 7, 2015

(54) INSERTER INSTRUMENT AND IMPLANT CLIP

(75) Inventors: Edward B. Zalenski, Lakeville, MA (US); Dale W. Frank, Fall River, MA (US); Michael D. Sorrenti, Middleboro, MA (US); Alexander Grinberg, Newton, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 2095 days.

(21) Appl. No.: 11/945,296

(22) Filed: Nov. 27, 2007

(65) Prior Publication Data

US 2008/0071293 A1 Mar. 20, 2008

Related U.S. Application Data

(62) Division of application No. 10/750,173, filed on Dec. 31, 2003, now Pat. No. 8,123,757.

(51) Int. Cl.
*A61B 17/56* (2006.01)
*A61F 2/46* (2006.01)
*A61B 19/00* (2006.01)

(52) U.S. Cl.
CPC .......... *A61F 2/4611* (2013.01); *A61B 2019/303* (2013.01); *A61B 2019/5437* (2013.01); *A61F 2002/4627* (2013.01); *A61F 2002/4628* (2013.01)

(58) Field of Classification Search
USPC ................ 606/99, 281, 86 A, 86 B; 623/17.11–17.16
See application file for complete search history.

(56) References Cited

U.S. PATENT DOCUMENTS

| 132,057 A | 10/1872 | Cooper et al. |
| 1,539,987 A | 2/1924 | Bell |

(Continued)

FOREIGN PATENT DOCUMENTS

| EP | 0 333 990 | 9/1989 |
| EP | 0535973 B1 | 4/1993 |

(Continued)

OTHER PUBLICATIONS

Krag et al., "An Internal Fixator for Posterior Application to Short Segments of the Thoacic, Lumbar, or Lumbosacral Spine," Clin. Ortho. & Related Res. 203:75-98 (1986).

(Continued)

*Primary Examiner* — David Bates
*Assistant Examiner* — Michael Araj
(74) *Attorney, Agent, or Firm* — Nutter McClennen & Fish LLP

(57) ABSTRACT

A method and apparatus assisting safe one-handed insertion of an implant. An implant implantation device has a frame which includes a trigger mechanism, an outer sleeve mechanically coupled to the frame, an inner shaft having a grabber for mechanically engaging an implant, the inner shaft slidably disposed within the outer sleeve, and a retaining element disposed over the inner shaft for directing the grabber toward a closed position. An implant clip has a first member, a second member pivotally coupled to the first member, a first implant holder pivotally coupled to the first member, the coupling causing the implant clip to have a closed position and an open position, and a second implant holder, the second implant holder pivotally coupled to the second member, a surface of the first implant holder and a surface of the second implant holder remaining substantially parallel to each other while the first member and the second member pivot between the closed position and the open position.

16 Claims, 18 Drawing Sheets

(56) References Cited

U.S. PATENT DOCUMENTS

| | | |
|---|---|---|
| 3,141,583 A | 7/1964 | Mapel |
| 3,752,161 A | 8/1973 | Bent |
| 3,835,860 A | 9/1974 | Garretson |
| 4,367,746 A | 1/1983 | Derechinsky |
| 4,512,345 A | 4/1985 | Green |
| 4,592,347 A | 6/1986 | Mahruki |
| 4,759,766 A | 7/1988 | Buettner-Janz et al. |
| 5,018,412 A | 5/1991 | Wylie, III |
| 5,222,973 A | 6/1993 | Sharpe et al. |
| 5,236,460 A | 8/1993 | Barber |
| 5,258,031 A | 11/1993 | Salib et al. |
| 5,300,081 A | 4/1994 | Young et al. |
| 5,314,477 A | 5/1994 | Marnay |
| 5,360,430 A | 11/1994 | Lin |
| 5,370,697 A | 12/1994 | Baumgartner |
| 5,383,888 A | 1/1995 | Zvenyatsky et al. |
| 5,401,269 A | 3/1995 | Buttner-Janz et al. |
| 5,425,773 A | 6/1995 | Boyd et al. |
| 5,431,654 A | 7/1995 | Nic |
| 5,431,658 A | 7/1995 | Mosovich |
| 5,443,514 A | 8/1995 | Steffee |
| 5,458,641 A | 10/1995 | Ramirez Jimenez |
| 5,486,185 A | 1/1996 | Freitas et al. |
| 5,505,732 A | 4/1996 | Michelson |
| 5,507,816 A | 4/1996 | Bullivant |
| 5,562,738 A | 10/1996 | Boyd et al. |
| 5,591,170 A | 1/1997 | Spievack et al. |
| 5,676,701 A | 10/1997 | Yuan et al. |
| 5,683,465 A | 11/1997 | Shinn et al. |
| 5,782,830 A | 7/1998 | Farris |
| 5,782,832 A | 7/1998 | Larsen et al. |
| 5,797,927 A | 8/1998 | Yoon |
| 5,851,207 A | 12/1998 | Cesarone |
| 5,873,886 A | 2/1999 | Larsen et al. |
| 5,895,428 A | 4/1999 | Berry |
| 5,899,941 A | 5/1999 | Nishijima et al. |
| 5,931,849 A | 8/1999 | Desvignes et al. |
| 5,938,678 A | 8/1999 | Zirps et al. |
| 5,989,291 A | 11/1999 | Ralph et al. |
| 6,019,792 A | 2/2000 | Cauthen |
| 6,063,121 A | 5/2000 | Xavier et al. |
| 6,066,174 A | 5/2000 | Farris |
| 6,099,550 A | 8/2000 | Yoon |
| 6,110,179 A | 8/2000 | Flivik et al. |
| 6,113,605 A | 9/2000 | Storer |
| 6,113,637 A | 9/2000 | Gill et al. |
| 6,146,421 A | 11/2000 | Gordon et al. |
| 6,159,215 A | 12/2000 | Urbahns et al. |
| 6,174,311 B1 * | 1/2001 | Branch et al. ............... 606/86 A |
| 6,179,874 B1 | 1/2001 | Cauthen |
| 6,227,079 B1 | 5/2001 | Liu |
| 6,228,118 B1 | 5/2001 | Gordon |
| 6,261,296 B1 * | 7/2001 | Aebi et al. ...................... 606/90 |
| 6,296,665 B1 | 10/2001 | Strnad et al. |
| 6,319,257 B1 | 11/2001 | Carignan et al. |
| 6,328,746 B1 | 12/2001 | Gambale |
| 6,358,268 B1 | 3/2002 | Hunt et al. |
| 6,368,350 B1 | 4/2002 | Erickson et al. |
| 6,371,986 B1 | 4/2002 | Bagby |
| 6,375,682 B1 | 4/2002 | Fleischmann et al. |
| 6,395,034 B1 | 5/2002 | Suddaby |
| 6,416,551 B1 | 7/2002 | Keller |
| 6,439,439 B1 | 8/2002 | Rickard et al. |
| 6,440,142 B1 | 8/2002 | Ralph et al. |
| 6,440,168 B1 | 8/2002 | Cauthen |
| 6,517,544 B1 | 2/2003 | Michelson |
| 6,517,580 B1 | 2/2003 | Ramadan et al. |
| 6,520,996 B1 | 2/2003 | Manasas et al. |
| 6,524,312 B2 | 2/2003 | Landry et al. |
| 6,527,804 B1 | 3/2003 | Gauchet et al. |
| 6,540,785 B1 | 4/2003 | Gill et al. |
| 6,562,074 B2 | 5/2003 | Gerbec et al. |
| 6,579,320 B1 | 6/2003 | Gauchet et al. |
| 6,599,292 B1 | 7/2003 | Ray |
| 6,599,294 B2 | 7/2003 | Fuss et al. |
| 6,599,295 B1 | 7/2003 | Tornier et al. |
| 6,616,671 B2 | 9/2003 | Landry et al. |
| 6,648,891 B2 | 11/2003 | Kim |
| 6,652,533 B2 | 11/2003 | O'Neil |
| 6,652,534 B2 | 11/2003 | Zucherman et al. |
| 6,660,006 B2 | 12/2003 | Markworth et al. |
| 6,663,637 B2 | 12/2003 | Dixon et al. |
| 6,692,501 B2 | 2/2004 | Michelson |
| 6,712,818 B1 | 3/2004 | Michelson |
| 6,740,087 B2 | 5/2004 | Knox |
| 7,011,683 B2 | 3/2006 | Antonelli et al. |
| 7,608,080 B2 | 10/2009 | Shipp et al. |
| 7,695,478 B2 | 4/2010 | Ralph et al. |
| 8,123,757 B2 | 2/2012 | Zalenski et al. |
| 2002/0035400 A1 | 3/2002 | Bryan et al. |
| 2002/0111679 A1 | 8/2002 | Zucherman et al. |
| 2002/0111681 A1 | 8/2002 | Ralph et al. |
| 2002/0111682 A1 | 8/2002 | Ralph et al. |
| 2002/0111683 A1 | 8/2002 | Ralph et al. |
| 2002/0111684 A1 | 8/2002 | Ralph et al. |
| 2002/0111685 A1 | 8/2002 | Ralph et al. |
| 2002/0111686 A1 | 8/2002 | Ralph et al. |
| 2002/0111687 A1 | 8/2002 | Ralph et al. |
| 2002/0116009 A1 * | 8/2002 | Fraser et al. ............... 606/99 |
| 2002/0128714 A1 | 9/2002 | Manasas et al. |
| 2002/0128715 A1 | 9/2002 | Bryan et al. |
| 2002/0161366 A1 | 10/2002 | Robie et al. |
| 2002/0161375 A1 | 10/2002 | Ralph et al. |
| 2002/0173813 A1 | 11/2002 | Peterson et al. |
| 2003/0033016 A1 | 2/2003 | Dees, Jr. |
| 2003/0040802 A1 | 2/2003 | Errico et al. |
| 2003/0060687 A1 | 3/2003 | Kleeman et al. |
| 2003/0065395 A1 | 4/2003 | Ralph et al. |
| 2003/0069586 A1 | 4/2003 | Errico et al. |
| 2003/0069643 A1 | 4/2003 | Ralph et al. |
| 2003/0074066 A1 | 4/2003 | Errico et al. |
| 2003/0074067 A1 | 4/2003 | Errico et al. |
| 2003/0074068 A1 | 4/2003 | Errico et al. |
| 2003/0074069 A1 | 4/2003 | Errico et al. |
| 2003/0074070 A1 | 4/2003 | Errico et al. |
| 2003/0074071 A1 | 4/2003 | Errico et al. |
| 2003/0074072 A1 | 4/2003 | Errico et al. |
| 2003/0074073 A1 | 4/2003 | Errico et al. |
| 2003/0074074 A1 | 4/2003 | Errico et al. |
| 2003/0074076 A1 | 4/2003 | Ferree et al. |
| 2003/0078664 A1 | 4/2003 | Ralph et al. |
| 2003/0078665 A1 | 4/2003 | Ralph et al. |
| 2003/0078666 A1 | 4/2003 | Ralph et al. |
| 2003/0083747 A1 | 5/2003 | Winterbottom et al. |
| 2003/0135275 A1 | 7/2003 | Garcia et al. |
| 2003/0135277 A1 | 7/2003 | Bryan et al. |
| 2003/0135278 A1 | 7/2003 | Eckman |
| 2003/0149482 A1 | 8/2003 | Michelson |
| 2003/0171813 A1 | 9/2003 | Kiester |
| 2003/0187454 A1 | 10/2003 | Gill et al. |
| 2003/0199872 A1 | 10/2003 | Markworth et al. |
| 2003/0216744 A1 | 11/2003 | Longhini et al. |
| 2004/0102850 A1 | 5/2004 | Shepard |
| 2004/0167534 A1 | 8/2004 | Errico et al. |
| 2004/0167537 A1 | 8/2004 | Errico et al. |
| 2004/0176773 A1 | 9/2004 | Zubok et al. |
| 2004/0215198 A1 | 10/2004 | Marnay et al. |
| 2004/0225295 A1 | 11/2004 | Zubok et al. |
| 2005/0015094 A1 | 1/2005 | Keller |
| 2005/0015095 A1 | 1/2005 | Keller |
| 2005/0021040 A1 | 1/2005 | Bertagnoli |
| 2005/0021042 A1 | 1/2005 | Marnay et al. |
| 2005/0027300 A1 | 2/2005 | Hawkins et al. |
| 2005/0033428 A1 | 2/2005 | Keller |
| 2005/0038511 A1 | 2/2005 | Martz et al. |
| 2005/0043740 A1 | 2/2005 | Haid, Jr. et al. |
| 2005/0043800 A1 | 2/2005 | Paul et al. |
| 2005/0055029 A1 | 3/2005 | Marik et al. |
| 2005/0055031 A1 | 3/2005 | Lim |
| 2005/0055098 A1 | 3/2005 | Zdeblick et al. |
| 2005/0071013 A1 | 3/2005 | Zubok et al. |
| 2005/0143749 A1 | 6/2005 | Zalenski et al. |

(56) References Cited

U.S. PATENT DOCUMENTS

2008/0167680 A1 7/2008 Voegele et al.
2010/0249795 A1 9/2010 DiMauro et al.

FOREIGN PATENT DOCUMENTS

| EP | 0630615 A1 | 12/1994 |
|---|---|---|
| FR | 2636227 | 3/1990 |
| FR | 2717068 | 9/1995 |
| WO | WO 97/38634 | 10/1997 |
| WO | WO 01/62136 | 8/2001 |

OTHER PUBLICATIONS

EP Search Report, from corresponding EP 09 17 3718.9, mailed Jul. 6, 2010.

* cited by examiner

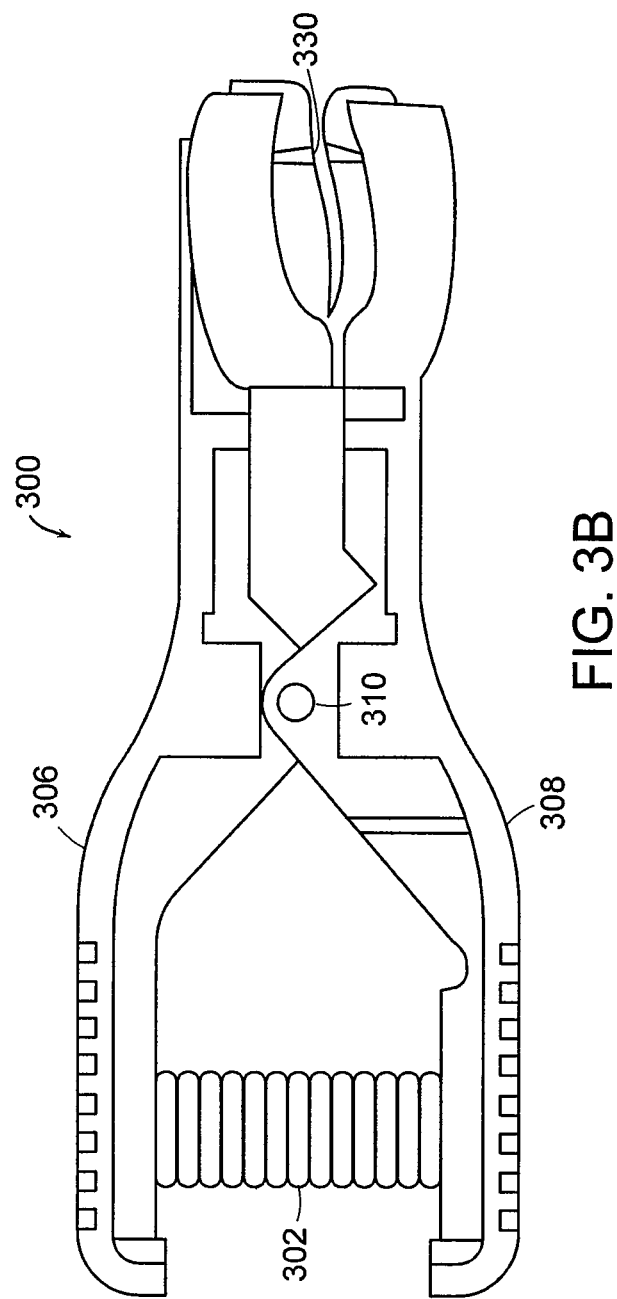

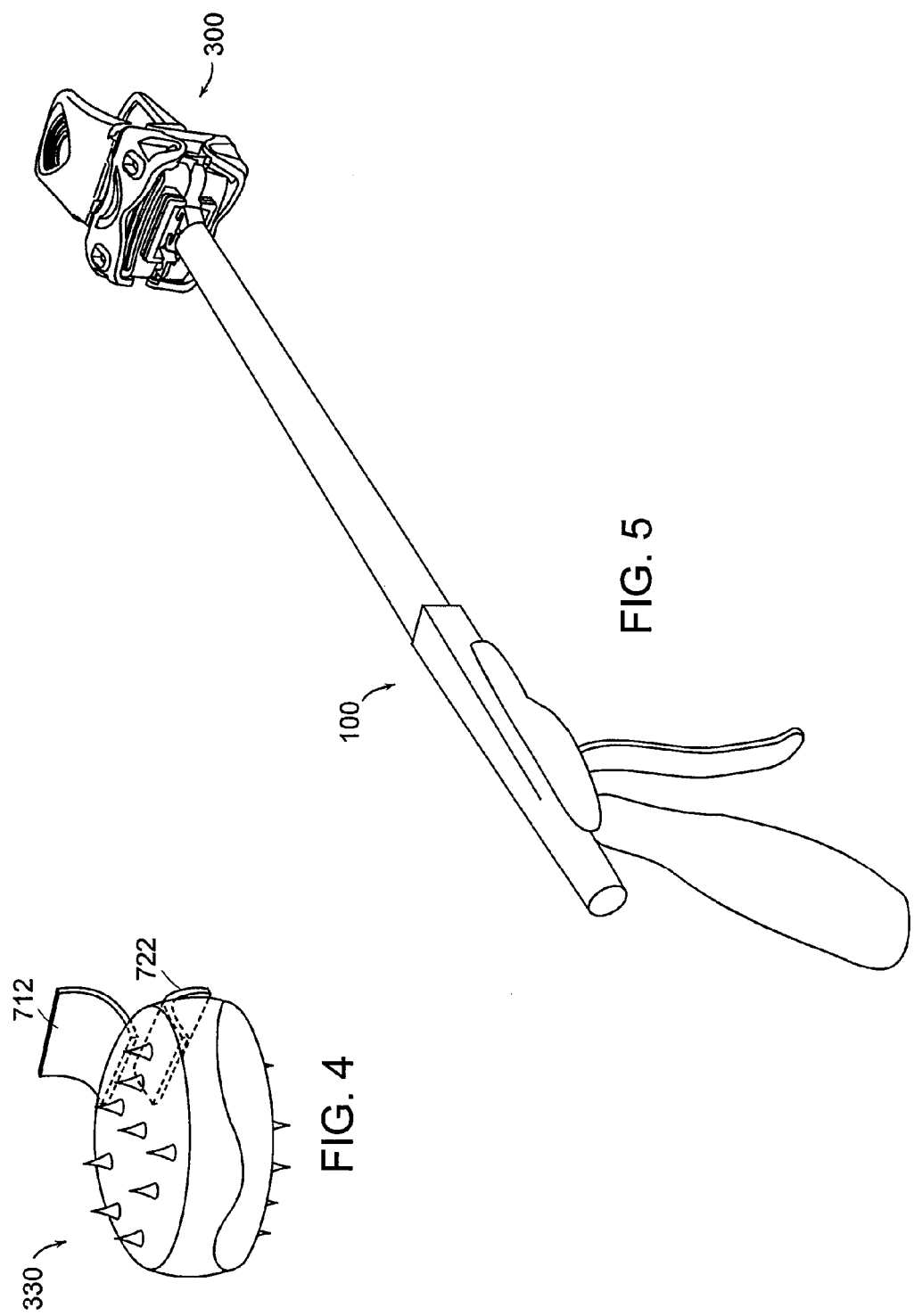

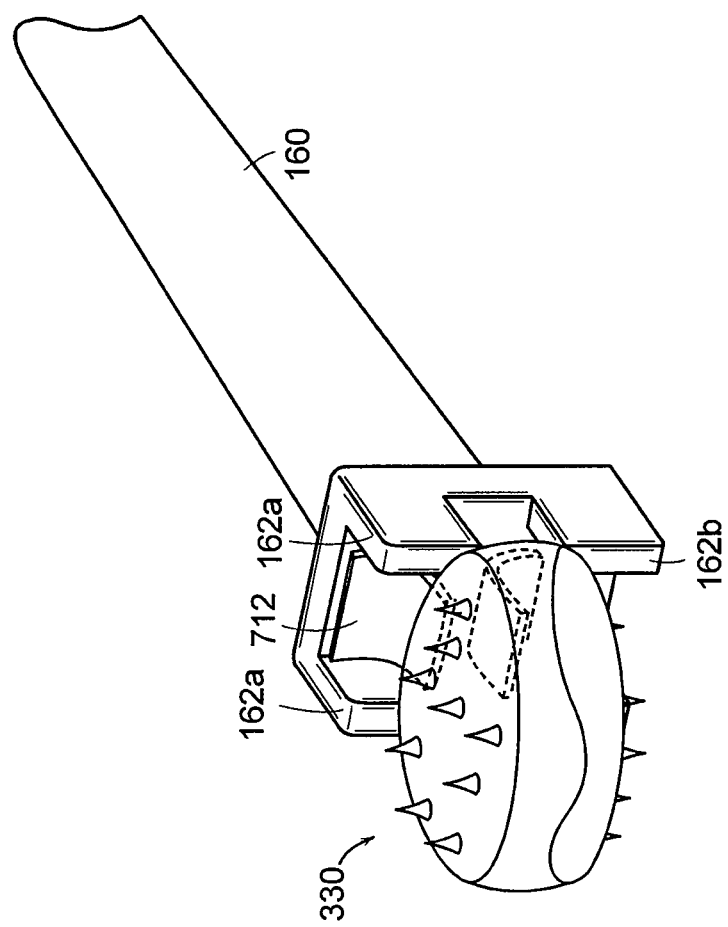

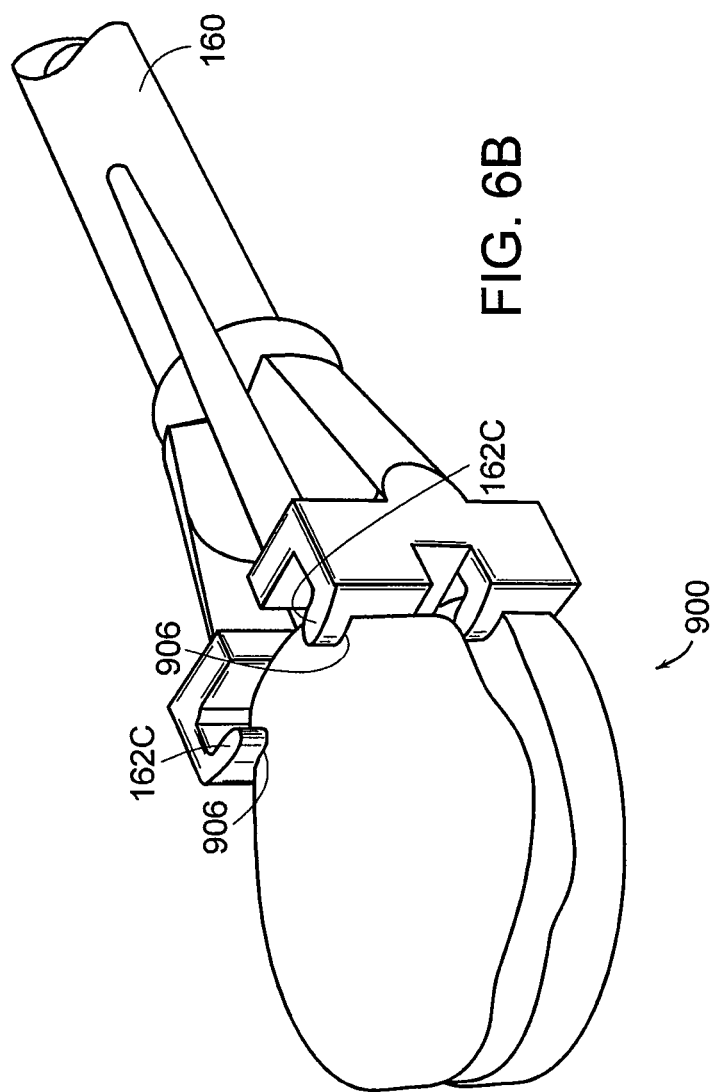

INSERTER INSTRUMENT AND IMPLANT CLIP

CROSS REFERENCE TO RELATED APPLICATIONS

This application is a divisional of U.S. application Ser. No. 10/750,173 filed Dec. 31, 2003, the entire contents of which are hereby incorporated herein by reference.

BACKGROUND OF THE INVENTION

Spinal surgery involves many challenges as the long-term health and mobility of the patient often depends on the surgeon's technique and precision. One type of spinal surgery involves the removal of a damaged disc that is located between adjacent vertebral bodies. Procedures are known in which the damaged disc is replaced with an artificial disc or spinal fusion cage.

The artificial disc or spinal fusion cage includes protrusions for engaging the adjacent vertebral bodies to aid in the initial fixation of the artificial disc or spinal fusion cage. These protrusions are often sharp and can injure the surgeon's hand, if contacted, during implantation.

The insertion of an article, such as the artificial disc or fusion cage, presents the surgeon with several challenges. The adjacent vertebral bodies collapse upon each other once the damaged disc is removed. These bodies must be separated to an extent sufficient to enable the placement of the prosthesis. However, if the vertebral bodies are separated, or distracted, to beyond a certain degree, further injury to the patient can occur. The artificial disc should also be properly positioned between the adjacent vertebral bodies. Over-insertion posteriorly, or under-insertion anteriorly of the prosthesis can lead to pain, postural problems and/or limited mobility or freedom of movement.

Specialized tools have been developed to facilitate the placement of devices, such as artificial discs, between adjacent vertebral bodies of a patient's spine. Among the known tools for performing such procedures are spinal distractors and insertion devices. However, use of these tools to distract the vertebral bodies and insert the artificial disc or spinal fusion cage can prove cumbersome.

Exemplary devices for installing prostheses and/or grafts between vertebral bodies are disclosed in U.S. Pat. Nos. 5,431,658 and 5,505,732. U.S. Pat. No. 5,431,658 discloses a facilitator device for the insertion of bone grafts between two adjacent vertebrae. The disclosed tool has two flat, tong-like guides that distract the vertebrae as a screw-type inserter forces the graft between the distracted vertebrae. U.S. Pat. No. 5,505,732 discloses an apparatus and a method of inserting implants. The intervertebral space is first distracted and a hollow sleeve having teeth at one end is then driven into the vertebrae that are adjacent the disc space. A drill is then passed through the hollow sleeve, removing the disc and the bone in preparation for receiving the implant, which is then inserted through the sleeve. These devices are both operated with two-hands and do not provide safety features for preventing injury to a surgeon.

Despite existing tools and technologies, there remains a need for an improved device to facilitate insertion of an artificial disc or a spinal fusion cage.

SUMMARY OF THE INVENTION

The invention is generally related to a method and apparatus for assisting in a safe one-handed insertion of an implant. An implant implantation device including (i) a frame which includes a trigger mechanism, (ii) an outer sleeve mechanically coupled to the frame, (iii) an inner shaft having a grabber for mechanically engaging an implant, the inner shaft slidably disposed within the outer sleeve and (iv) a retaining element for directing the grabber toward a closed position. The grabber can be removably coupled to the inner shaft. The retaining element can be a spring.

Optional elements can include a knob, a drag adjustment screw, at least one protrusion, and a depth control member. The knob can be mechanically coupled to the outer sleeve for causing the outer sleeve and the inner shaft to be rotated about the frame. The drag adjustment screw can provide tension between the trigger mechanism and the inner shaft. The at least one protrusion can be located on the outer sleeve for slidably engaging a distraction instrument. The depth control member can be slidably coupled to the outer sleeve for providing a predetermined insertion depth of the implant.

The grabber is provided to hold the implant during insertion of the implant between the vertebrae. The grabber includes grabber tips for mechanically engaging the implant. The grabber tips can have a variety of shapes. For example, the grabber tips can be dovetailed in shape or can include a first pair of slots for engaging a first tab of the implant and a second pair of slots for engaging a second tab of the implant. The first pair of slots can be different in size from the second pair of slots. A sizing slot can be located between the first pair of slots and second pair of slots to allow for a variation of tab and grabber slot dimensional differences.

The grabber also can include at least one marking to identify a position of the implant in relationship to the patient. The marking can be a pin located on a surface of the grabber. The marking can be a plurality of machined slots on a surface of the grabber.

There is also provided an implant clip for aligning an implant endplate radially, providing a lordotic angle for implantation, packaging the implant, holding the implant during the implant sterilization process, and protecting the surgeon from being cut by protrusions on a surface of the implant. The implant clip, includes (i) a first member; (ii) a second member pivotally coupled to each other, the coupling causing the implant clip to have a closed position and an open position, (iii) a first implant holder pivotally coupled to the first member, and (iv) a second implant holder, the second implant holder pivotally coupled to the second member, a surface of the first implant holder and a surface of the second implant holder remaining substantially parallel to each other while the first member and the second member pivot between the closed position and the open position. The first member and the second member can be shells. The implant clip can also include a spring for directing the implant clip toward a closed position.

Each holder can define a depression, where each depression is angled with respect to its holder. Each depression can also be made from a conformable material. The second holder can include a pair of pins that slidably engage a respective pair of cylindrical cavities in the first holder, thereby causing the surface of each holder to remain substantially parallel to each other while the first member and the second member pivot between the closed position and the open position. Alternatively, the first holder and the second holder can include a respective pin and a respective cylindrical cavity that slidably engage each other, thereby causing the surface of each holder to remain substantially parallel to each other while the first member and the second member pivot between the closed position and the open position. Each holder can also include at least one alignment protrusion for aligning of an implantation instrument with the implant clip.

A method of inserting the implant into an intervertebral space includes (i) loading an implant in an implant clip, (ii) mechanically engaging an implantation instrument to the implant and (iii) removing the implant from the implant clip. The implant can be an artificial disc or spinal fusion cage.

Loading an implant in an implant clip includes (i) opening the implant clip, (ii) inserting the implant into the implant clip, and (iii) closing the implant clip.

Mechanically engaging the implantation instrument to the implant includes (i) opening a grabber located on an end of the implantation instrument, (ii) aligning the grabber with the implant, and (iii) closing the grabber to mechanically engage the grabber to the implant.

The method further includes (iv) distracting a prepared disc space with a distraction instrument, (v) inserting the implant into the prepared disc space with the implantation instrument, (vi) releasing the implant from the implantation instrument, and (vii) removing the implantation instrument and distraction instrument.

Inserting the implant into the prepared disc space includes aligning the implantation instrument with the distraction instrument.

The invention has many advantages. For example, the invention provides safe one-handed insertion of an implant into a prepared disc space. The invention reduces the amount of time required to complete the surgical procedure. The invention also provides for various manipulations of the implant without physically contacting the implant. For example, the invention can align an endplate of the implant radially and provide a lordotic angle for implantation, the invention can be used for packaging the implant, and the invention can be used to hold the implant during the implant sterilization process.

BRIEF DESCRIPTION OF THE DRAWINGS

FIG. 3B shows a side view of the implant clip of FIG. 3A.

FIG. 4 shows a perspective view of an artificial disc.

FIG. 5 shows a perspective view of the insertion instrument of FIG. 1 engaged to an implant enclosed in the implant clip of FIG. 3A.

FIG. 6A shows perspective view of the artificial disc of FIG. 4 engaged to the grabber of FIG. 2A.

FIG. 6B shows perspective view of another type of implant engaged to the grabber of FIGS. 2B and 2C.

DETAILED DESCRIPTION OF THE INVENTION

Figure 1A:
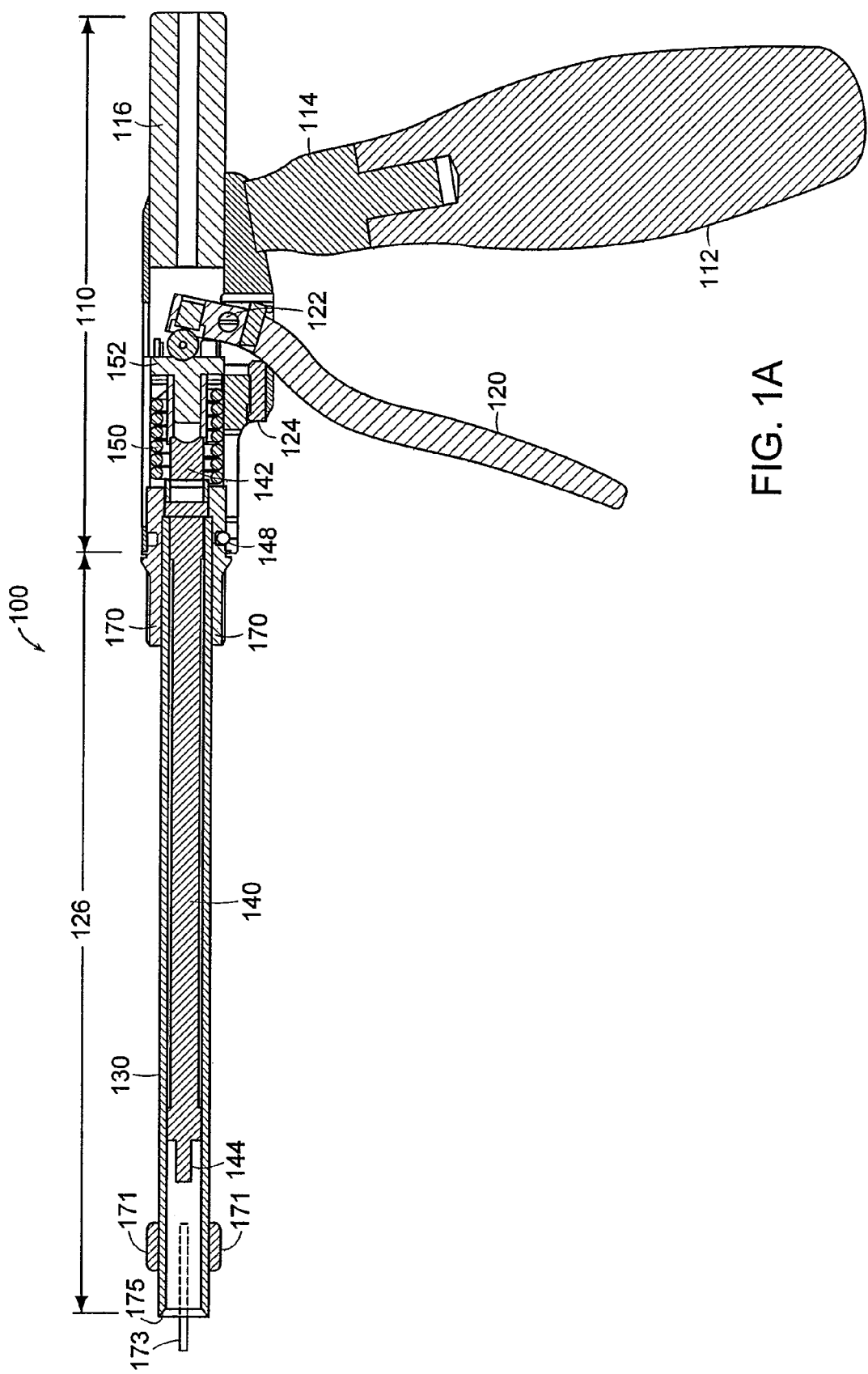
FIG. 1A shows a cross-sectional view of an insertion instrument of the present invention.

The foregoing and other objects, features and advantages of the invention will be apparent from the following more particular description of preferred embodiments of the invention, as illustrated in the accompanying drawings in which like reference characters refer to the same parts throughout the different views. The same number appearing in different drawings represents the same item. The drawings are not necessarily to scale, with emphasis instead being placed upon illustrating the principles of the invention.

Figure 1B:
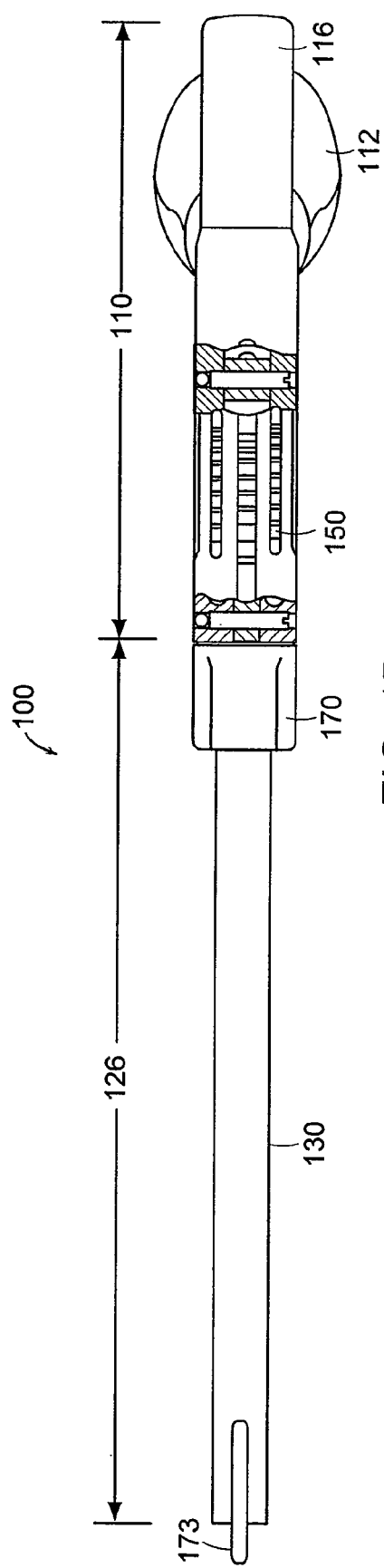
FIG. 1B shows a plan view of the insertion instrument of FIG. 1A.
Figure 2A:
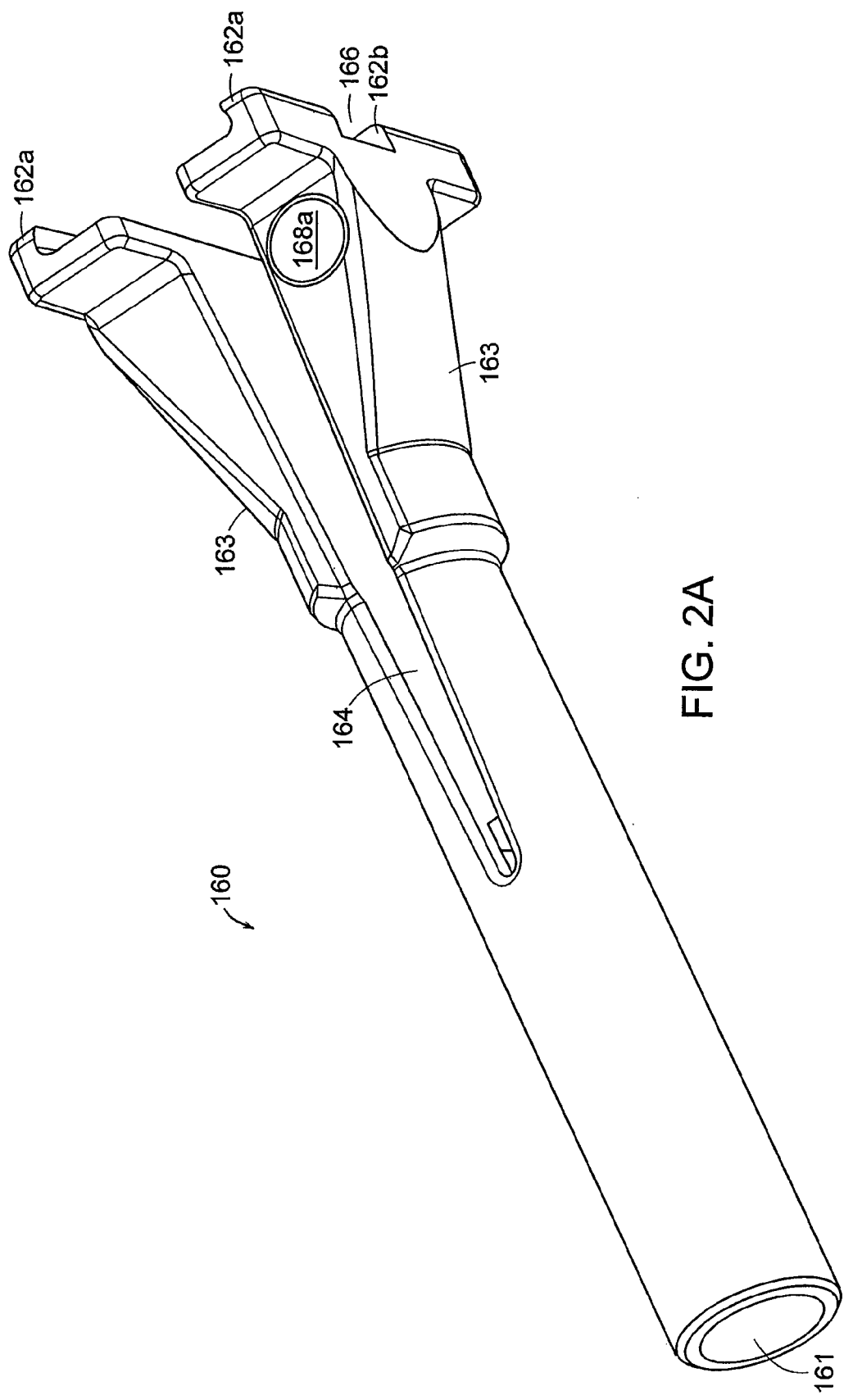
FIG. 2A shows a perspective view of one embodiment of a grabber of the present invention.
Figure 2B:
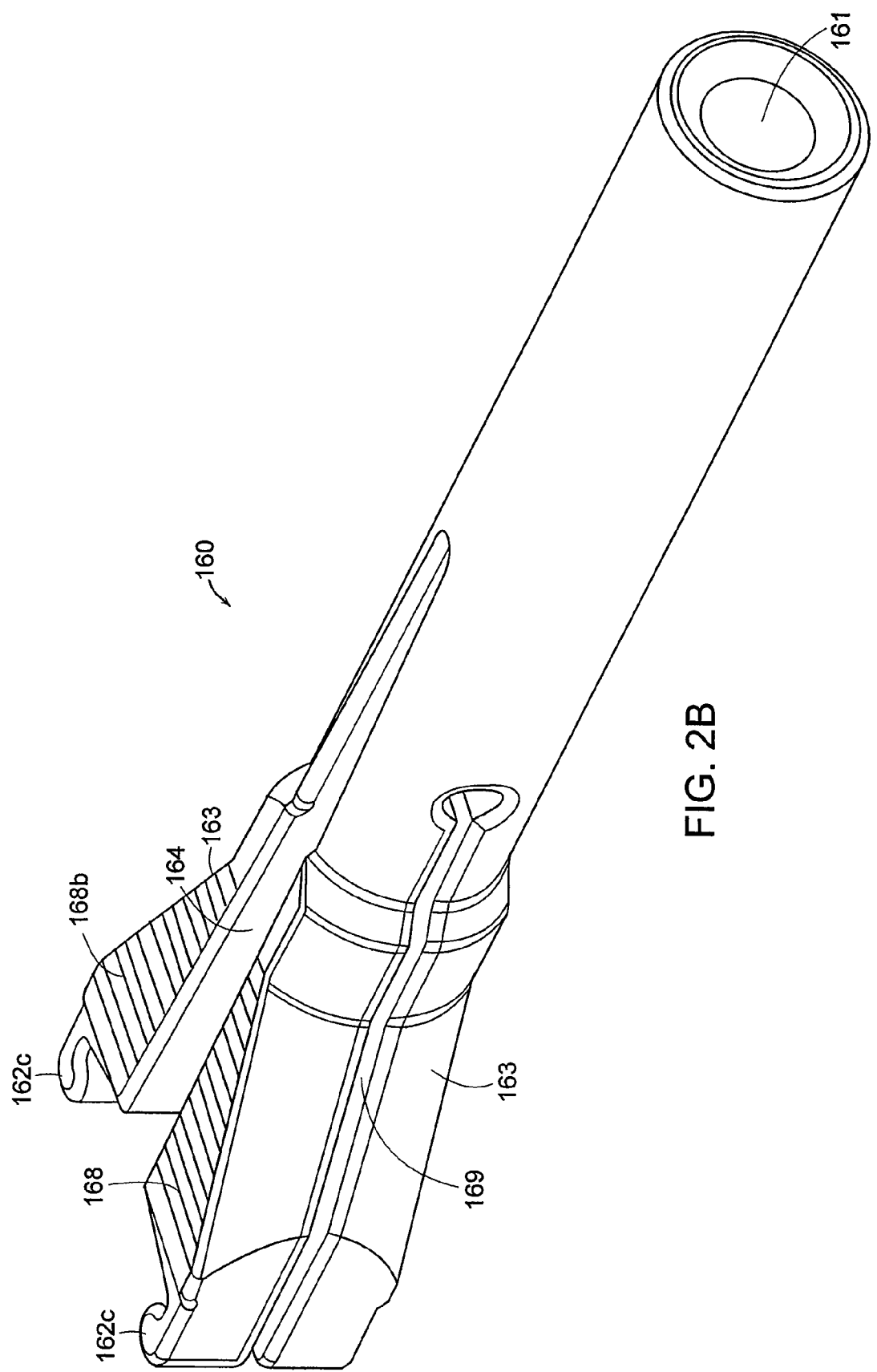
FIG. 2B shows a perspective view of another embodiment of a grabber of the present invention.
Figure 2C:
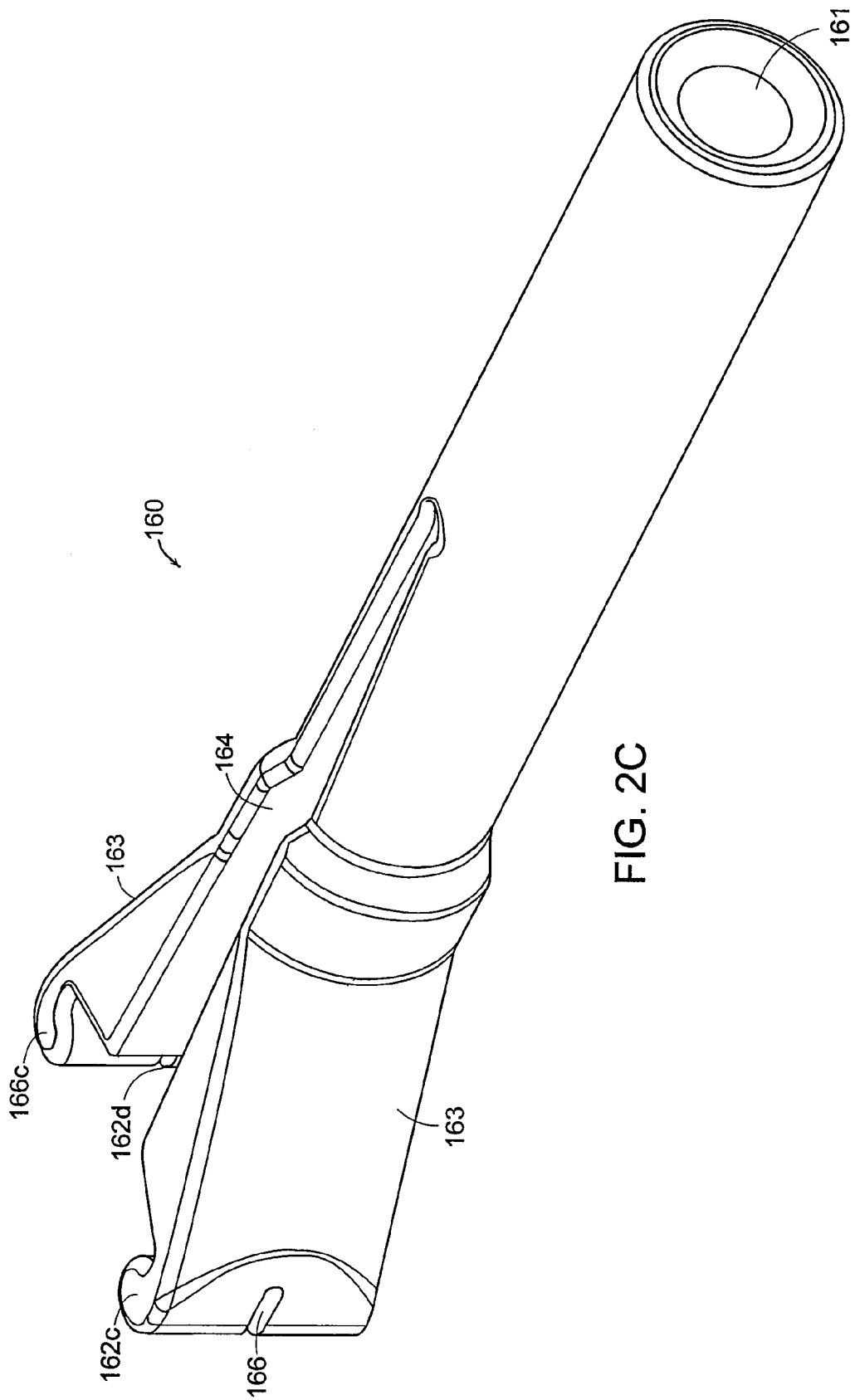
FIG. 2C shows a perspective view of yet another embodiment of a grabber of the present invention.

In general, the present invention is related to apparatus and method for safely inserting an implant into a prepared disc space. The implant can be an artificial disc or spinal fusion cage. Referring to FIGS. 1A and 1B, insertion instrument 100 is shown in a side cross-sectional view and a plan view, respectively. Insertion instrument 100 includes frame or driver body assembly 110, actuator assembly 126 and grabber 160 (FIG. 2A-2C). Insertion instrument 100 is a normally closed device, that is, grabber 160 is normally substantially contained within actuator assembly 126.

Figure 7:
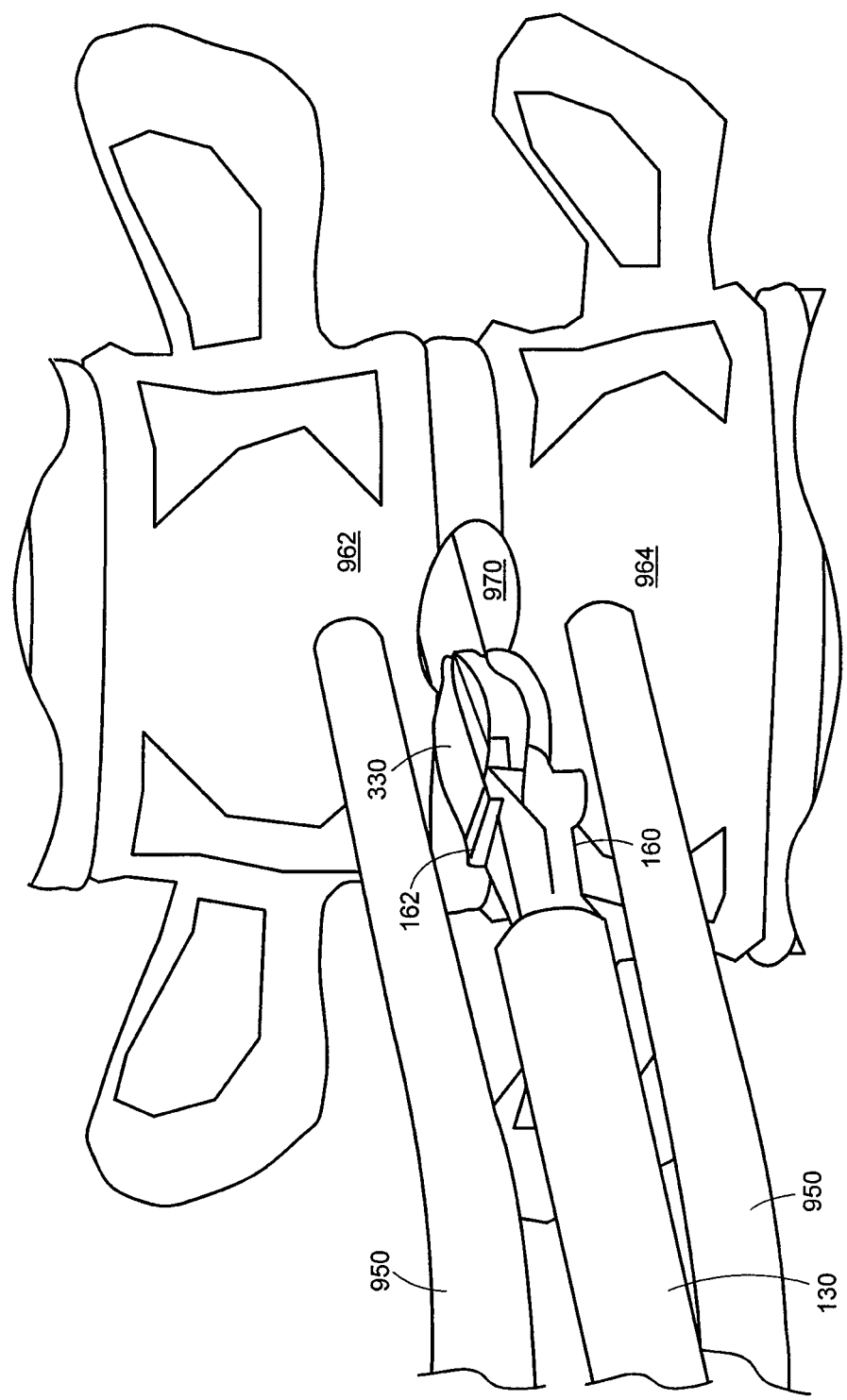
FIG. 7 shows a perspective view of the artificial disc of FIG. 4 being inserted into a prepared disc space using the insertion instrument if FIG. 1.

Actuator assembly 126 includes outer sleeve 130, inner shaft 140, and retaining pin 148. Outer sleeve 130 includes a tapered end 175 which slidably engages tapers 163 on grabber 160 (FIG. 2A-2C), allowing for compression and expansion of the grabber 160 when in use. Inner shaft 140 includes female threaded end 142 and male threaded end 144. Female threaded end 142 mates with spring retaining screw 152 and male threaded end 144 mates with grabber 160. Internal compression spring 150 is fastened to actuator assembly 126 and held in place by spring retaining screw 152. Once actuator assembly 126 is assembled, it is inserted into driver body assembly 110 and retained within assembly 110 with retaining pin 148. Optional knob 170 can be mechanically attached to outer sleeve 130 to allow outer sleeve 130 and inner shaft 140 to rotate about driver body assembly 110. Optional guides 171 can be attached to outer sleeve 130 to slidably mate with spinal disc distraction instrument 950 (FIG. 7). Depth control member 173 can also be fixedly or slidably attached on outer sleeve 130 for providing a predetermined insertion depth of the implant.

Driver body assembly 110 includes handle 112, handle transition 114, strike boss 116, trigger mechanism 120, and pivot pin 122. Trigger mechanism 120 can be any type of trigger mechanism known in the art. Trigger mechanism 120 pivots about pivot pin 122 in driver body assembly 110. When trigger mechanism 120 is "squeezed" toward handle 112, grabber 160 (FIG. 2A-2C) extends from actuator assembly 126 and expands to release or attach to an implant. When trigger mechanism 120 is released, grabber 160 recedes into actuator assembly 126 and compresses, thereby engaging the implant or returning to its normally closed position. Optional drag adjustment screw 124 is rotatably coupled to driver body assembly 110 for adjusting the drag force between trigger mechanism 120 and spring retaining screw 152 of actuator assembly 126.

FIGS. 2A-2C show various grabbers 160 of the present invention. Each grabber 160 includes grabber tips 162 for mechanically engaging the implant. Grabber tips 162 may be various shapes and sizes depending upon implant selection. As shown, grabber tips 162 may be slot shaped 162a, 162b or dovetailed shaped 162c, 162d. Grabber tips 162 can engage implants having multiple heights. It should be understood grabber tips 162 can be any shape which can engage any type of implant. In an alternative embodiment, inner shaft 140 and grabber 160 can be one embodiment.

Each grabber 160 includes female threaded hole 161 for mating to male threaded end 144 of inner shaft 140 of actuator assembly 126. It should be understood that any means known in the art can be used to attach grabber 160 to inner shaft 140.

Each grabber 160 includes tapers 163 and relatively long expansion/compression slot 164 to allow grabber 160 to expand and compress during use. FIGS. 2A-2C show grabber 160 in the expanded position. Each grabber 160 also includes sizing slot 166 to allow for a variation of tab and grabber slot dimensional differences. Expansion/compression slot 169 (FIG. 2B) is an alternative embodiment of sizing slot 166.

Cephalad markers 168 can be included on a surface of grabber 160 to allow the user to determine the position of the implant. Markers 168 can be pin 168a or machined slots 168b.

FIGS. 3A-3I show details of implant clip 300. Implant clip 300 can be used to align the implant radially and provide a lordotic angle for implantation, can be used for implant packaging, can be used to hold the implant during the implant sterilization process, and can protect the surgeon from being cut by protrusions on the surface of the implant. Implant clip 300 includes a pair of symmetrical shells 306, 308, superior implant holder 312, inferior implant holder 318, and spring 302. In another embodiment, shells 306, 308 can be any type of member which can hold the implant.

Each shell 306, 308 includes spring holder 301, pivot member 310, pivot hole 311, and a pair of holder holes 314. Each pivot member 310 snappingly and pivotally engages pivot hole 311 of opposing shells 306, 308. Spring 302 is connected between shells 306, 308 and maintained in place by spring holders 301. Spring 302 maintains implant clip 300 in a normally closed position, as shown in at least FIGS. 3A and 3B.

In one embodiment, as shown in FIGS. 3A, 3D, 3F, and 3H, superior implant holder 312 includes a pair of alignment protrusions 316, a pair of protrusion members 317, a pair of position poles 324, and implant depression 315. Inferior implant holder 318 includes a pair of alignment protrusions 322, a pair of protrusion members 317, a pair of position holes 326, and implant depression 321. In another embodiment, as shown in FIGS. 3C and 3G, superior implant holder 312 and inferior implant holder 318 can be symmetrical for ease of production.

Figure 3A:
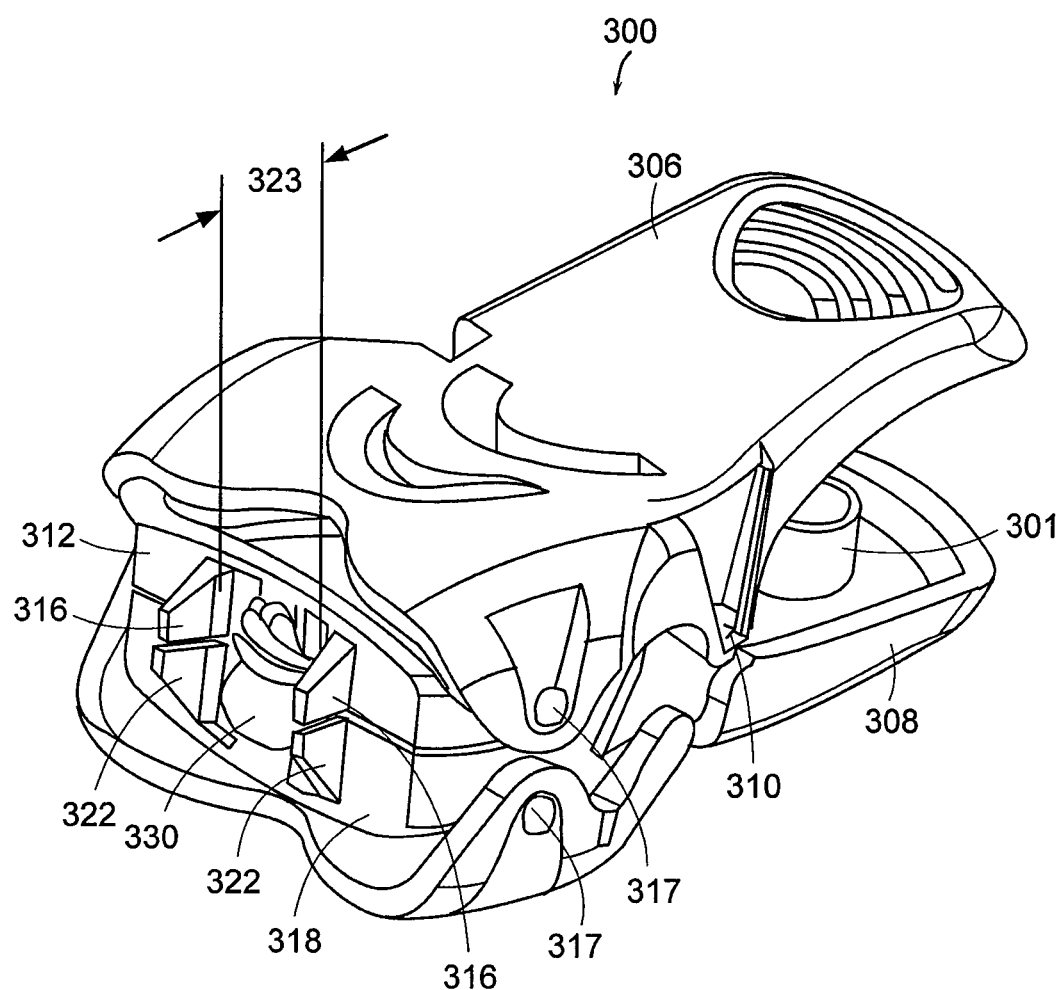
FIG. 3A shows a perspective view of one embodiment of an implant clip of the present invention.
Figure 3C:
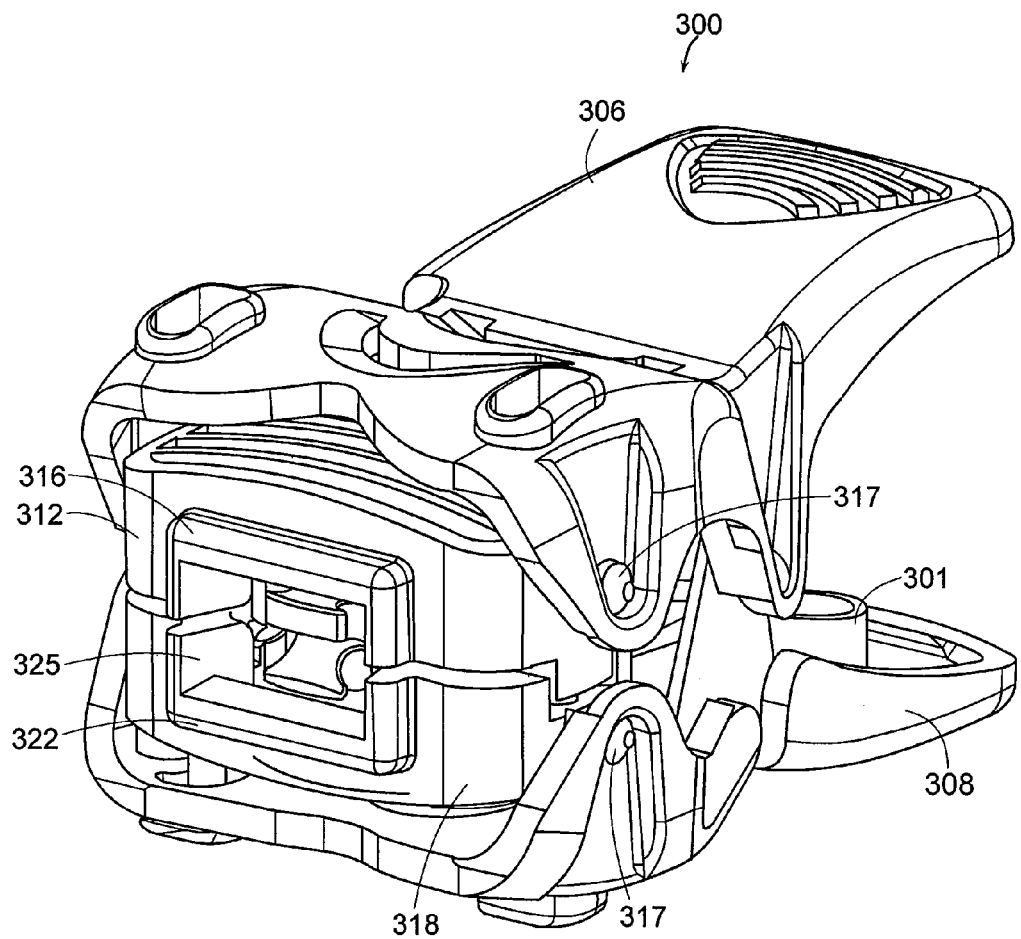
FIG. 3C shows a perspective view of another embodiment of an implant clip the of present invention.
Figure 3D:
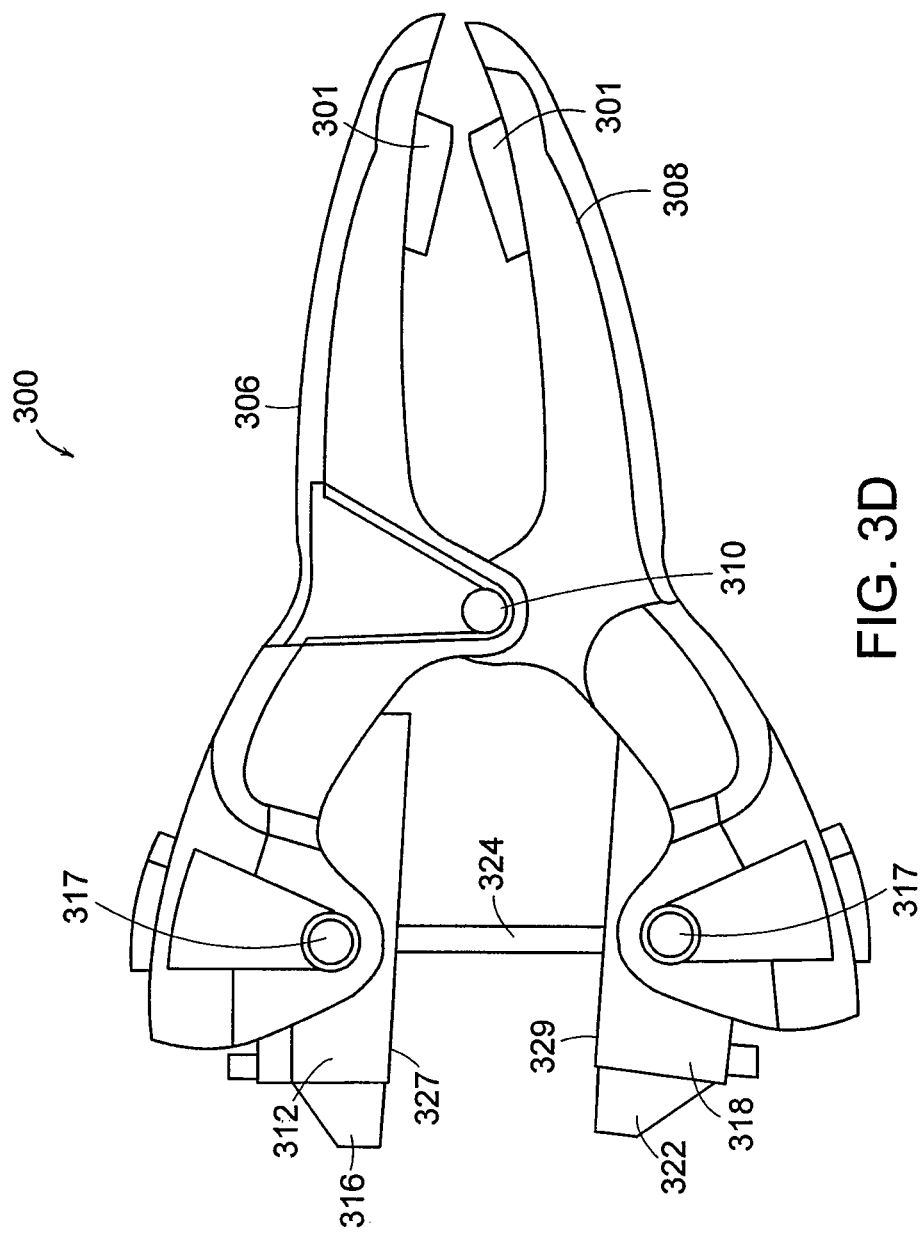
FIG. 3D shows a side view of the implant clip of FIG. 3B in an open position.
Figure 3E:
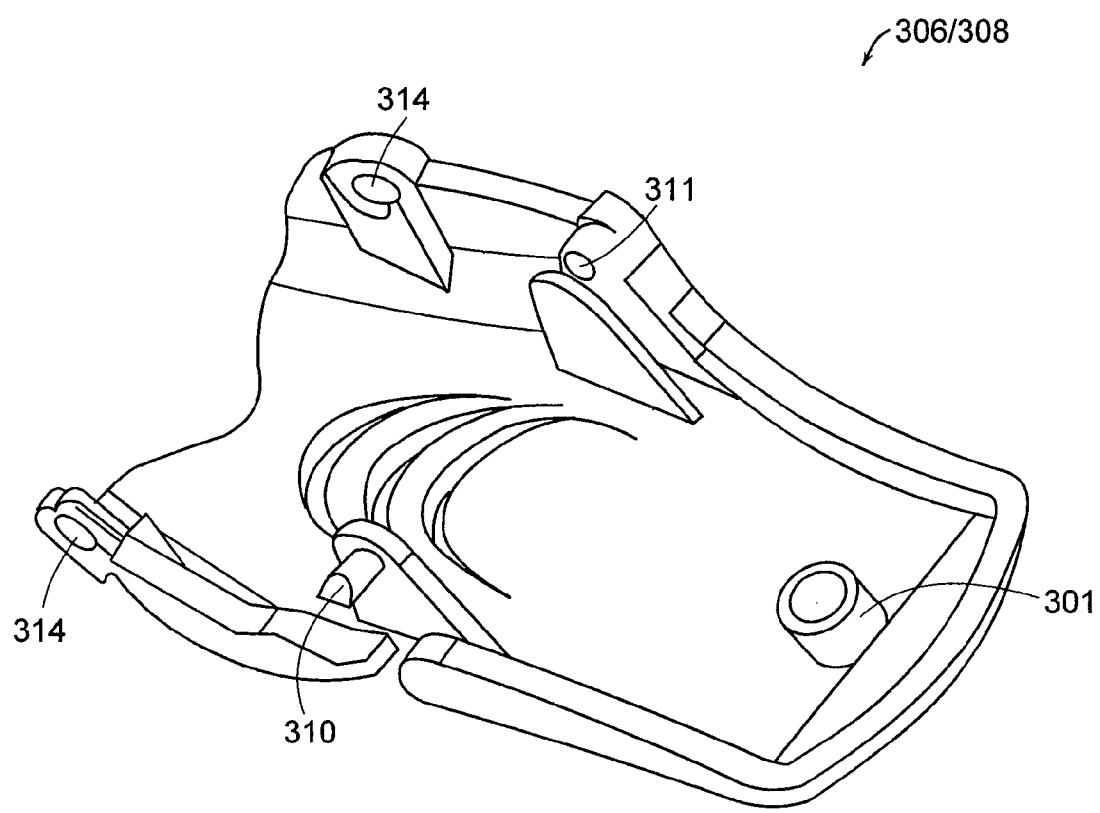
FIG. 3E shows a perspective view of a shell of the implant clip of FIG. 3A.
Figure 3F:
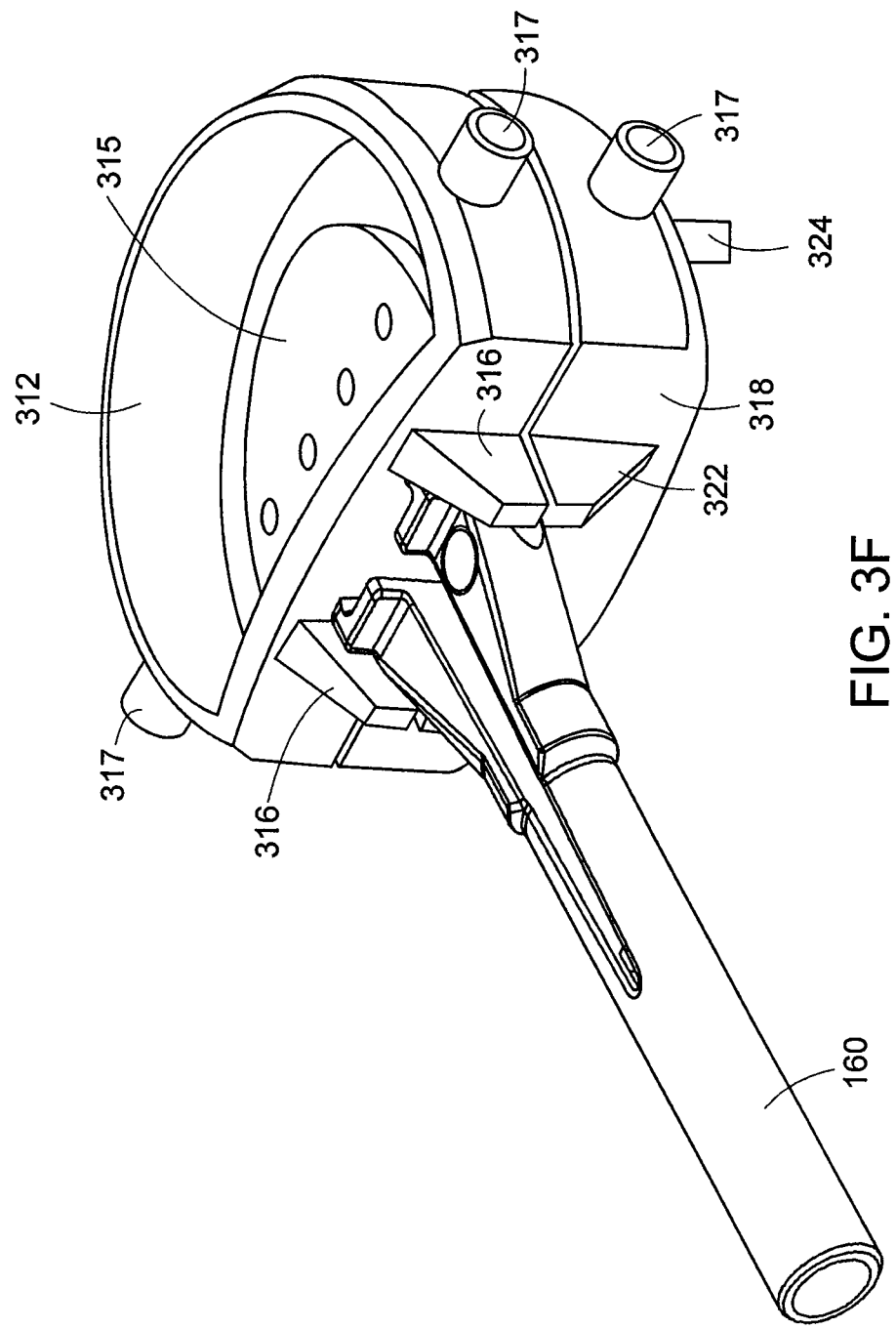
FIG. 3F shows a perspective view of a grabber aligned with a pair of implant holders.
Figure 3G:
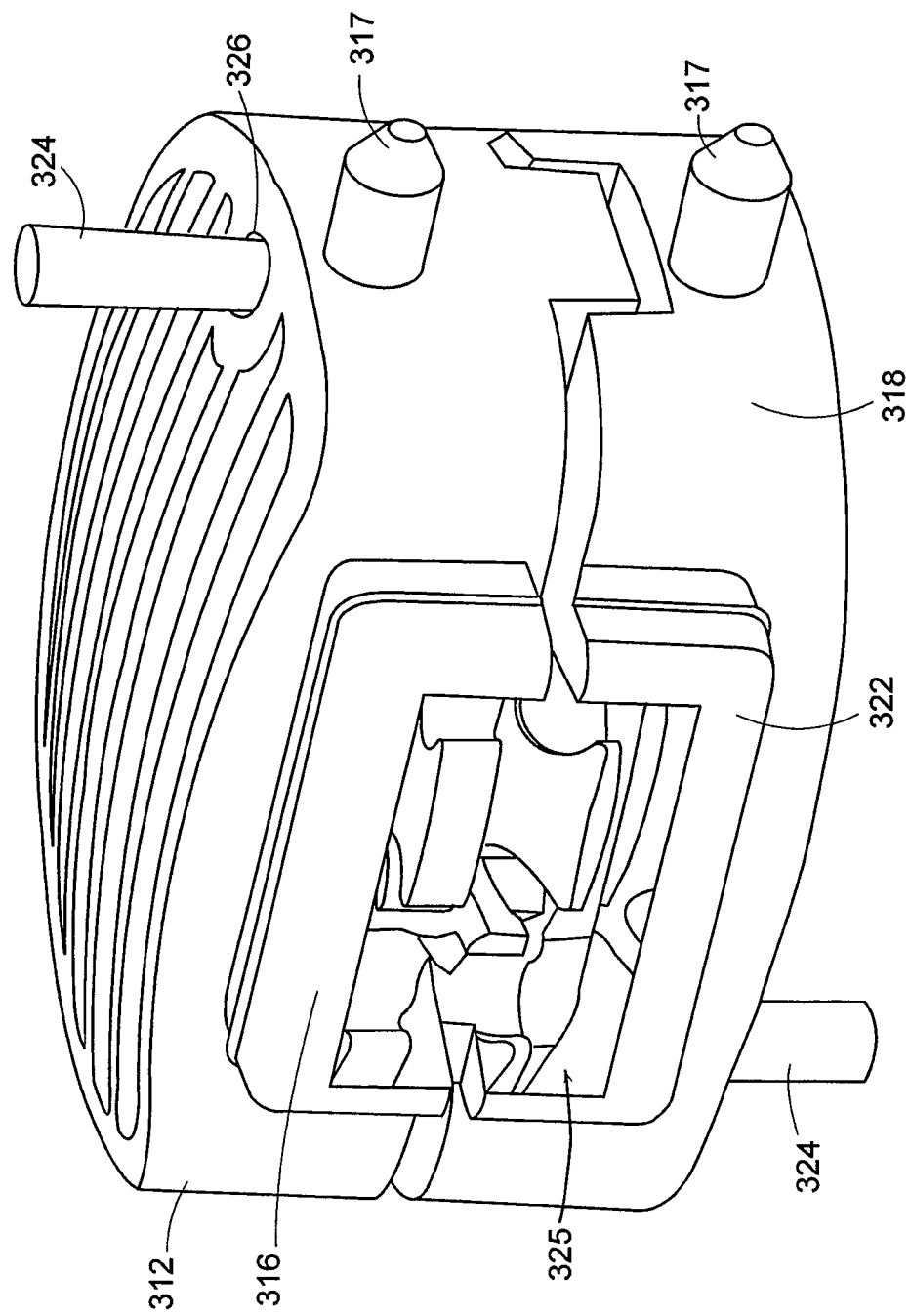
FIG. 3G shows a perspective view of a pair of implant holders of the implant clip of FIG. 3C.
Figure 3H:
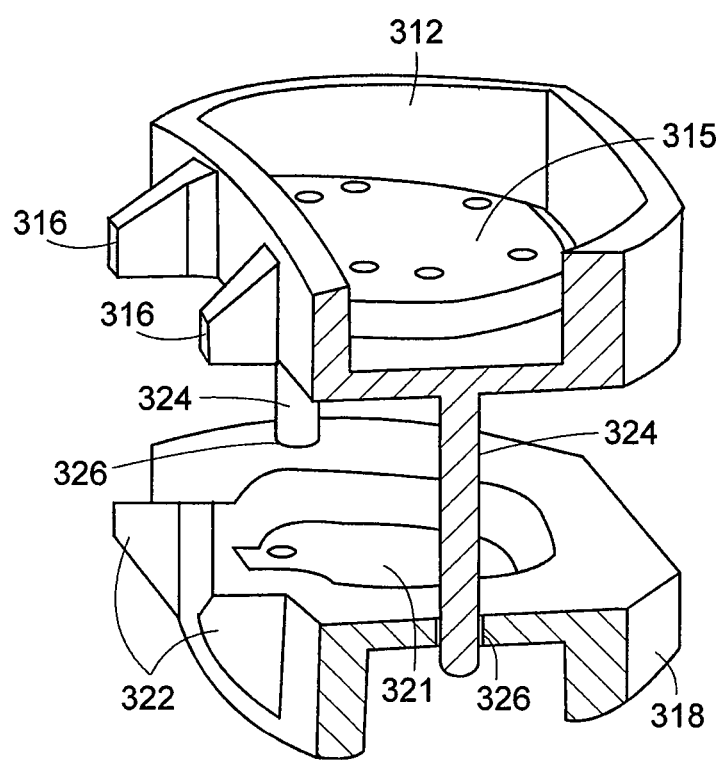
FIG. 3H shows a cutaway perspective view of a pair of implant holders of the implant clip of FIG. 3A.

Position poles 324 slidably engage position holes 326 such that surfaces 327, 329 remain substantially parallel to each other while implant clip 300 moves between a closed position as shown in FIGS. 3A-3C and an open position as shown in FIG. 3D. It should be understood that any method can be employed to maintain holders 312, 318 parallel to each other. Once each holder 312, 318 is slidably engaged to each other, protrusion member 317 of each holder 312, 318 snappingly and pivotally engages a pair of holder holes 314 in respective shells 306, 308. Shells 306, 308 can be made from a nylon-based plastic or other material known in the art which allows shells 306, 308 to be snappingly engaged to each other. Holders 312, 318 are typically made from injection moldable, gamma sterilizable hard plastics, such as Radel, Carbon Fiber, Peek, and Acrylonitrile Butadiene Styrene (ABS). However, holders 312, 318 can be made from any material known in the art which can protect the implant from damage.

Implant depressions 315, 321 are made to accept a plurality of implants of different shapes and sizes. Implant depressions 315, 321 can be angled with respect to holders 312, 318 to provide a lordotic angle for the implant. Implant depressions 315, 321 can also be conformable to accept a plurality of implants. Alternatively, implant depressions 315, 321 can be rigid to accept individual respective implants.

Alignment protrusions 316, 322 of implant clip 300 cause proper alignment of grabber 160 (FIGS. 2A-2C) with engagement protrusions 712, 722 of artificial disc 330 (FIG. 4). Alignment protrusions 316, 322 can form alignment slot 323 as shown in at least FIG. 3A or an alignment window 325 as shown in FIGS. 3C and 3G.

Figure 3I:
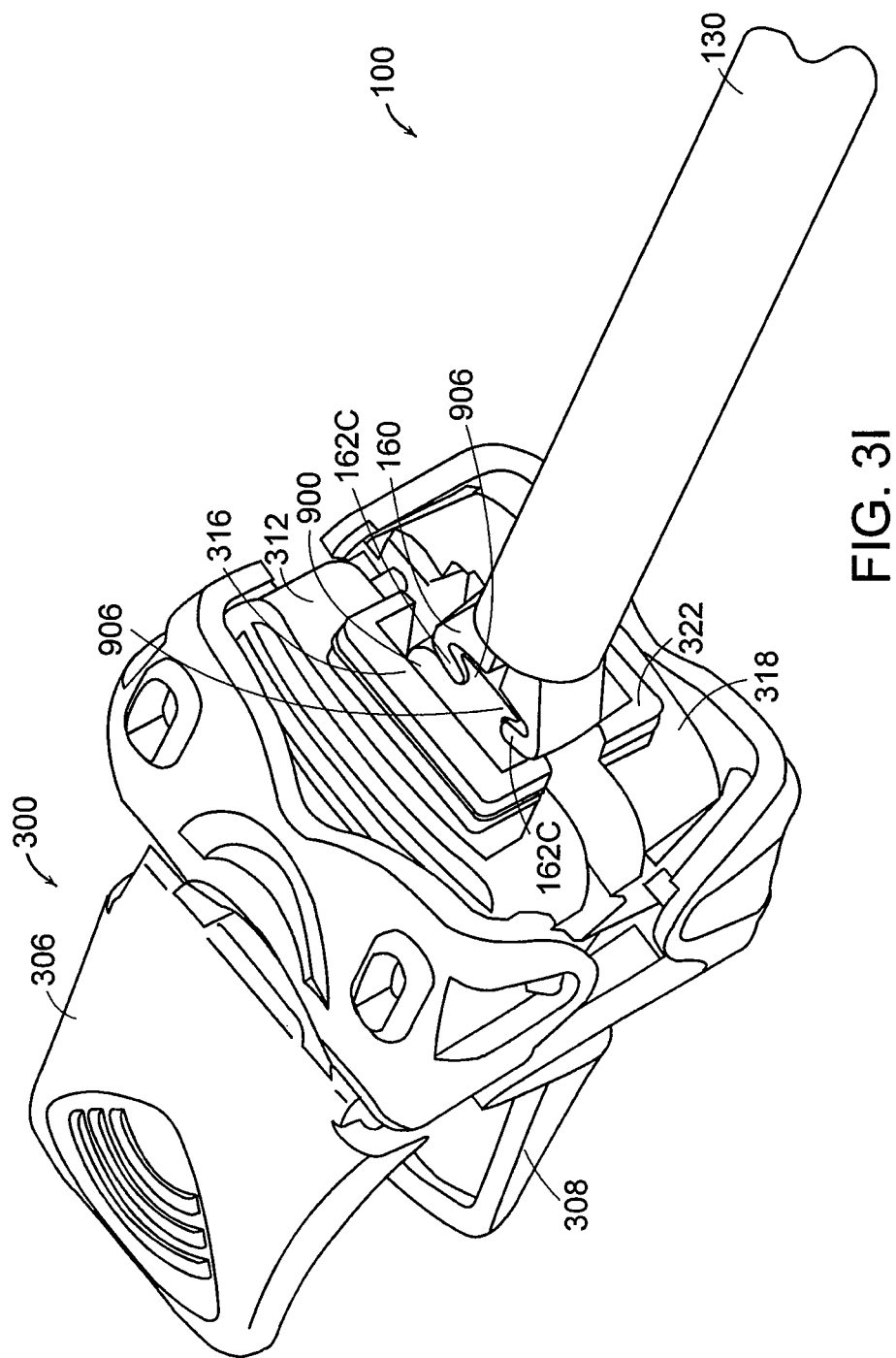
FIG. 3I shows a perspective view of the implant clip of FIG. 3B attached to the grabber of FIG. 2C.

FIG. 3I shows a perspective view of the implant clip of FIG. 3B attached to the grabber of FIG. 2C. Grabber 160 is in a closed position (i.e., trigger released) within outer sleeve 130 of insertion instrument 100. Grabber tips 162c are shown engaged to engagement indents 906 on artificial disc 900 which is contained within holders 312, 318 of implant clip 300.

The operation of insertion instrument 100 and implant clip 300 will be explained with reference to the figures. Although reference is made to an artificial disc 330, its principles are applicable to spinal fusion cages.

In operation, a user opens (FIG. 3C) implant clip 300 by depressing and holding opposite portions of shells 306, 308 at opposite ends of spring 302 (FIG. 3B) to an open position as shown in FIG. 3D. Opened clip 300 is placed over a selected artificial disc 330, causing implant holders 312, 318 to engage artificial disc 330 when shells 306, 308 are released.

In one embodiment, the user aligns grabber 160 (FIG. 2A) of implantation instrument 100 with alignment slot 323 on implant clip 300. Once aligned, the user squeezes trigger mechanism 120 (FIG. 1) on implantation instrument 100, thereby causing grabber tips 162a, 162b to be inserted over engagement tabs 712, 722 on artificial disc 330 (FIG. 4). Once grabber tips 162 are inserted over engagement tabs 712, 722, the user releases trigger mechanism 120, causing grabber tips 162 to engage engagement tabs 712, 722 on artificial disc 330 as shown in FIG. 5. The user removes implant clip 300 from artificial disc 330 by opening and removing implant clip 300 from the now engaged artificial disc 330, as shown in FIG. 6A.

In another embodiment, the user aligns grabber 160 (FIGS. 2B and 2C) of implantation instrument 100 with alignment window 325 on implant clip 300. Once aligned, the user squeezes trigger mechanism 120 (FIG. 1) on implantation instrument 100, thereby causing grabber tips 162c, 162d to be inserted over engagement indents 906 on artificial disc 900 (FIGS. 3I and 6B). Once grabber tips 162 are inserted over engagement indents 906, the user releases trigger mechanism 120, causing grabber tips 162 to engage engagement indents 906 on artificial disc 900 (FIG. 3I). The user removes implant clip 300 from artificial disc 900 by opening and removing implant clip 300 from the now engaged artificial disc 900, as shown in FIG. 6B.

As shown in FIG. 7, distraction instrument 950 is inserted over pins (not shown) that are secured into vertebral bodies 962, 964. Artificial disc 330 is passed between the forks of distraction instrument 950 using implantation instrument 100 (FIGS. 1A-1B). In an alternate embodiment, guides 170 on insertion instrument 100 slidably engage slots in the forks of distraction instrument 950 to help the user guide artificial disc 330 into prepared disc space 970. Once artificial disc 330 is in a desired location within prepared disc space 970, the user squeezes trigger mechanism 120 (FIG. 1A) which releases artificial disc 330 in prepared disc space 970. The user can determine the desired position by observing cephalad markers 168 (FIGS. 3A-3B) located on a surface of grabber 160. In an alternative embodiment, implantation instrument 100 can include depth control member 173 (FIG. 1A) such that artificial disc 330 can be inserted into prepared disc space 970 at a predetermined depth.

Implantation instrument 100 and distraction instrument 950 are removed, causing superior vertebra 962 and inferior vertebra 964 to engage artificial disc 330.

EQUIVALENTS

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of inserting an implant, comprising the steps of:
   (i) loading an implant in an implant clip;
   (ii) mechanically engaging an implantation instrument, the implantation instrument having an extended position and a closed position, to the implant by moving the implantation instrument from the extended position to the closed position in engagement with the implant; and
   (iii) removing the implant from the implant clip while the implantation instrument remains engaged to the implant;
   wherein the implant is an artificial disc and the step of loading an implant in an implant clip includes aligning the implant radially with respect to the implant clip;
   wherein the step of loading an implant in an implant clip includes providing a lordotic angle to the implant for implantation; and
   wherein the implant clip includes holders and implant depressions, and the implant depressions are angled with respect to the holders in order to provide the lordotic angle during the loading of the implant in the implant clip.

2. The method of claim 1, wherein the step of loading an implant in an implant clip includes:
   (i) opening the implant clip;
   (ii) inserting the implant into the implant clip; and
   (iii) closing the implant clip.

3. The method of claim 1, wherein the step of mechanically engaging the implantation instrument to the implant includes:
   (i) opening a grabber located on an end of the implantation instrument;
   (ii) aligning the grabber with the implant; and
   (iii) closing the grabber to mechanically engage the grabber to the implant.

4. The method of claim 1, further including the steps of:
   (iv) distracting a prepared disc space with a distraction instrument;
   (v) inserting the implant into the prepared disc space with the implantation instrument;
   (vi) releasing the implant from the implantation instrument; and
   (vii) removing the implantation instrument and distraction instrument.

5. The method of claim 4, wherein the step of inserting the implant into the prepared disc space includes aligning the implantation instrument with the distraction instrument.

6. The method of claim 1, wherein the implant is an artificial disc or a spinal fusion cage.

7. The method of claim 6, further comprising (iv) after the implant has been removed from the implant clip, using the implantation instrument mechanically engaged to the implant to insert the implant into a prepared disc space.

8. The method of claim 1, wherein the implant is an artificial disc having engagement tabs and the implantation instrument includes grabber tips and the step of mechanically engaging the implant to the implantation instruments includes inserting the grabber tips over the engagement tabs.

9. A method of inserting an implant, comprising the steps of:
   (i) loading an implant in an implant clip;
   (ii) mechanically engaging an implantation instrument to the implant; and
   (iii) removing the implant from the implant clip while the implantation instrument remains engaged to the implant
   wherein the step of mechanically engaging the implantation instrument to the implant includes:
   (a) opening a grabber located on an end of the implantation instrument;
   (b) aligning the grabber with the implant; and
   (c) closing the grabber to mechanically engage the grabber to the implant.

10. The method of claim 9, wherein the step of loading an implant in an implant clip includes:
    (i) opening the implant clip;
    (ii) inserting the implant into the implant clip; and
    (iii) closing the implant clip.

11. The method of claim 9, further including the steps of:
    (iv) distracting a prepared disc space with a distraction instrument;
    (v) inserting the implant into the prepared disc space with the implantation instrument;
    (vi) releasing the implant from the implantation instrument; and
    (vii) removing the implantation instrument and distraction instrument.

12. The method of claim 11, wherein the step of inserting the implant into the prepared disc space includes aligning the implantation instrument with the distraction instrument.

13. The method of claim 9, further comprising (iv) after the implant has been removed from the implant clip, using the implantation instrument mechanically engaged to the implant to insert the implant into a prepared disc space.

14. The method of claim 9, wherein the implant is an artificial disc and the step of loading an implant in an implant clip includes aligning the implant radially with respect to the implant clip.

15. The method of claim 14, wherein the step of loading an implant in an implant clip includes providing a lordotic angle to the implant for implantation.

16. The method of claim 15, wherein the implant clip includes holders and implant depressions, and the implant depressions are angled with respect to the holders in order to provide the lordotic angle during the loading of the implant in the implant clip.

* * * * *